(12) United States Patent
Tao

(10) Patent No.: US 7,132,837 B1
(45) Date of Patent: Nov. 7, 2006

(54) SYSTEM AND METHOD FOR MEASURING CONDUCTIVITY ON MOLECULAR LEVEL

(75) Inventor: Nongjian Tao, Scottsdale, AZ (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 10/929,134

(22) Filed: Aug. 26, 2004

(51) Int. Cl.
*G01R 27/08* (2006.01)
*G01N 27/453* (2006.01)

(52) U.S. Cl. ............................. 324/693; 204/547
(58) Field of Classification Search ............... 324/693, 324/661, 664, 425; 204/556, 547
See application file for complete search history.

(56) References Cited

U.S. PATENT DOCUMENTS

| | | | |
|---|---|---|---|
| 5,945,832 A * | 8/1999 | Harvey et al. ............. | 324/693 |
| 6,737,286 B1 * | 5/2004 | Tao et al. ..................... | 438/17 |
| 6,919,128 B1 * | 7/2005 | McCreery ................... | 428/333 |
| 6,977,511 B1 * | 12/2005 | Patel et al. ................. | 324/661 |
| 2005/0121328 A1 * | 6/2005 | Shirakashi et al. .......... | 205/96 |
| 2005/0126913 A1 * | 6/2005 | Burke et al. ................ | 204/547 |
| 2005/0138804 A1 * | 6/2005 | Hasegawa et al. ........... | 29/847 |

\* cited by examiner

*Primary Examiner*—Anjan Deb
(74) *Attorney, Agent, or Firm*—Robert D. Atkins; Quarles & Brady Streich Lang LLP

(57) ABSTRACT

A conductivity measurement system measures conductivity of molecules. A substance to be measured is applied to the first and second electrodes. A potential is applied across the electrodes. A computer-controlled motion controller moves a first electrode relative to a second electrode in discrete steps. In a first step, the electrodes are brought together in physical contact to form a plurality of molecular junctions. The electrodes are separated by a first distance which breaks a first molecular junction. The electrodes are separated by a second distance which breaks a second molecular junction. A conductivity measure is taken at each step. The process of separating the electrodes continues until conductivity measure is zero. The conductivity of one molecule corresponds to a last non-zero conductivity measurement prior to a zero conductivity measurement.

12 Claims, 4 Drawing Sheets

SYSTEM AND METHOD FOR MEASURING CONDUCTIVITY ON MOLECULAR LEVEL

STATEMENT REGARDING FEDERALLY-SPONSORED RESEARCH OR DEVELOPMENT

The U.S. Government has a paid-up license in the present invention and the right in limited circumstances to require the patent owner to license others on fair and reasonable terms as provided by the terms of Defense Advanced Research Projects Agency (DARPA) Grant No. DE-FG03-01ER45943 awarded by the Department of Defense.

FIELD OF THE INVENTION

The present invention relates in general to nanotechnology and, more particularly, to a system and method of measuring conductivity on the molecular level.

BACKGROUND OF THE INVENTION

Many practical devices used in the industry and in various applications of technology continue to dramatically reduce in feature size. In the field of nanotechnology, device miniaturization has reached the boundary of the molecular level. Work is on-going to achieve practical devices, in areas such as microelectronics, chemical sensors, and bio-sensors, which are quantified in terms of numbers of molecules.

In the process of designing nanotechnology devices, there is a need for instrumentation and techniques of qualifying, measuring, and characterizing such devices. Analysis tools such as the Scanning Tunneling Microscope (STM) and Atomic Force Microscope (AFM), electromigration fabricated electrodes, break junctions, mercury drops, nanopores, nanorods, and cross-wire tunneling junctions, have been used to understand the characteristics and behavior of nanotechnology devices. The ability to measure and record physical phenomena at the molecular level is essential to understanding the attributes and behavior of molecules and advancing basic research into practical applications. For example, these tools have been used to gain knowledge about electron transport in molecules. It is important to fundamental nanotechnology research and development to be able to accurately and repeatable measure and characterize the conductivity or resistivity of one or more molecules. Understanding the conductivity of a molecule reveals significant insight into its physical and chemical makeup and interaction with other molecules.

In the work toward developing analysis tools aimed at quantifying molecular conductivity, a variety of techniques have been tried with varying degrees of success. In one approach, a molecule is anchored to a conducting substrate with covalent bonding. A STM tip or conducting AFM tip can be placed over the top of the molecule to measure the current through the molecule between the tip and the substrate. While the molecule can form a reproducible contact to the substrate via the covalent bond, the tip-molecule contact conductance remains undefined, which makes it difficult to determine the conductivity of the molecule itself.

Another related approach is to cap a metal particle onto the molecule. Again, the contact conductance between the metal particle and the tip is undefined. Moreover, the molecules prepared for the STM/AFM measurements are often imbedded in matrix of other molecules, which often prevents the molecule from binding to analyte molecules for sensor applications.

In break junctions, a pair of electrodes is formed separated with a molecular scale gap. The two electrodes originate by breaking a metal wire on the substrate to create the gap. By bridging the gap with molecules terminated with linkers that can bind to the electrodes, a molecular junction is formed which permits a measure of the electron transport properties of the molecular junction.

In a similar approach, the process of electromigration forms a molecular scale gap between two electrodes by passing an electrical current through a thin wire to break the wire into two electrodes via electromigration effect. When molecules are present during the electromigration process, a molecular junction is formed in which molecules bridge across two electrodes.

In a cross wire tunneling junction, a metal is first coated with a layer of molecules, and a second wire is placed over the first wire in perpendicular direction. A molecular junction can be formed by carefully controlling the separation between the two wires.

In an electrode-molecular film-electrode junction, the electrical properties of molecules can be measured by sandwiching a layer of the molecules between two electrodes. The layer of molecules is placed on a flat electrode by self-assembly or by using the Langmuir-Blodgett method. A metal film is evaporated on top of the molecular layer. For nanopore and nanorod molecular junctions, the nanopore and the nanorod junctions are formed in a similar manner with the electrode-molecular film-electrode sandwich structure formed in the nanoscale pores in a SiN membrane or alumina templates. In the case of nanorod method, molecular junctions are first formed in the pores of membrane templates electrochemically. The membranes are then dissolved to leave molecular junctions floating in solution. The molecular junctions are trapped electrically to the gaps between electrodes to allow conductivity measurement of the molecular junctions.

Unfortunately, for each of the above known approaches, it is difficult to accurately and repeatably determine how many molecules are involved in the molecular junctions. The conductivity test may involve one molecule or many molecules; there is no way to be certain as to specifically how many molecules are bridging the electrodes. Also, there is uncertainty as to how, or even if, the molecules are joined to the electrodes. In many tests, the electrodes are not properly coated or protected as required for electrical measurement in aqueous solutions. Finally, these processes rely on electron beam lithography or other expensive fabrication procedures, which may not be practical or available to users.

A need exists to accurately and repeatably measure the electrical conductivity of a determinable number of one or more molecules.

SUMMARY OF THE INVENTION

In one embodiment, the present invention is a conductivity measurement system for measuring conductivity of molecules comprising first and second electrodes. A motion controller is coupled to the first electrode. A power supply having first and second conductors is coupled for applying a potential between the first and second electrodes. A conductivity measuring device is coupled to the first or second conductor for measuring conductivity between the first and second electrodes.

In another embodiment, the present invention is a conductivity measurement system comprising first and second electrodes adapted for receiving a substance to be measured, wherein the first electrode is moveable with respect to the second electrode. A conductivity measuring device is coupled to the first or second electrode for measuring the conductivity of a molecule of the substance to be measured as the first and second electrodes separate.

In another embodiment, the present invention is a method of measuring conductivity of a molecule comprising providing first and second electrodes, applying a potential between the first and second electrodes, applying a substance to be measured to the first and second electrodes, moving the first electrode relative to the second electrode, and measuring conductivity of the substance to be measured at a plurality of distances between the first and second electrodes.

In another embodiment, the present invention is a method of measuring conductivity of a molecule comprising applying a substance to be measured to first and second electrodes, moving the first electrode relative to the second electrode, and measuring conductivity of the substance to be measured at a plurality of distances between the first and second electrodes, wherein the conductivity of one molecule corresponds to a last non-zero conductivity measurement prior to a zero conductivity measurement.

DETAILED DESCRIPTION OF THE DRAWINGS

The present invention is described in one or more embodiments in the following description with reference to the Figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

In the field of nanotechnology, many devices have been miniaturized to the molecular level. Nanotechnology has produced practical devices, in areas such as microelectronics, chemical sensors, and bio-sensors, which can be described in terms of numbers of molecules. The ability to measure and record physical characteristics at the molecular level is essential to understanding the attributes and behavior of molecules and advancing basic research and development into practical applications.

One important design tool is the ability to accurately and repeatedly measure conductivity or resistivity, and current-voltage (I-V) characteristics, of a determinable number of one or more molecules. The process of isolating a given number of molecules will be described. The number of molecules isolated for measurement may be one, two, three, or more. Understanding the conductivity of a molecule reveals significant information as to its identification, chemical makeup, and physical interaction with other molecules.

The ability to measure and control electron transport, in terms of conduction or resistance, through a single molecule is an important tool in designing, developing, and testing nanotechnology devices. In one example, an electronic device may be realized as one molecule or a small number of molecules. With many analysis tools, it is difficult to make contact, take measurements, and otherwise work at the molecular level. The present invention provides the ability to measure conductivity of one or more molecules in an accurate and repeatable fashion. The conductivity measure will provide significant information about the device being measured that would otherwise be difficult to obtain.

Figure 1:
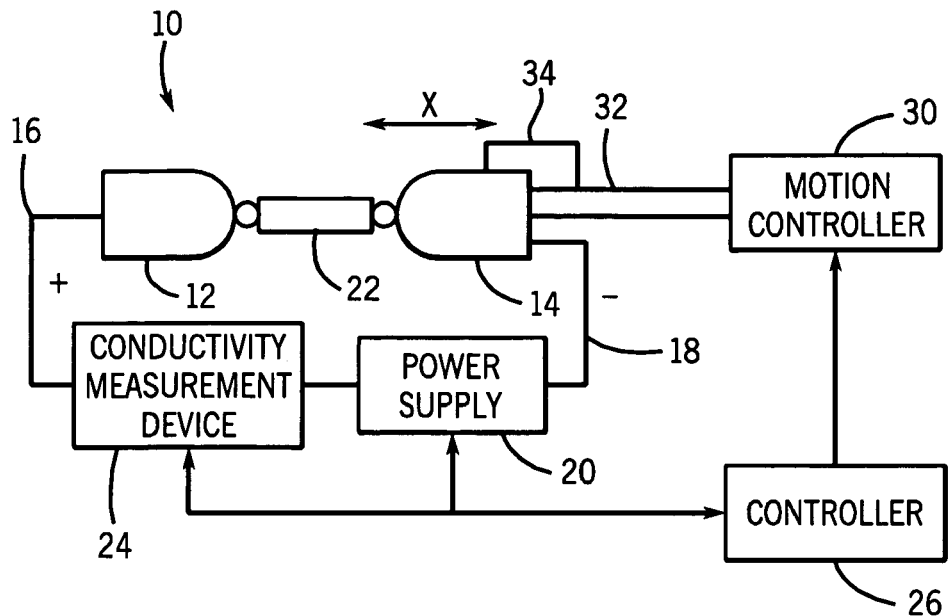
FIG. 1 illustrates a conductivity measurement system.

In FIG. 1, a conductivity measurement system 10 is shown including probe electrode 12 and probe electrode 14. In one embodiment, probe electrodes 12–14 are made of gold (Au) and may come to a sharp point or be rounded on the contact end. Further detail of probe electrodes 12–14 is provided in U.S. Pat. No. 6,737,286, which is incorporated herein by reference. Electrodes 12–14 are electrically connected by conductors 16 and 18 to power supply 20 which provides a potential across the electrodes. The potential may be a one volt or less DC voltage with polarity as shown. A molecular structure 22 is connected between electrodes 12 and 14. Molecular structure 22 comprises one or more molecules of a substance to be measured disposed across the gap between the electrodes. A complete series conduction path is made from the positive terminal of power supply 22, through electrode 12, molecular structure 22, and electrode 14, back to the negative terminal of power supply 22. With a voltage applied across electrodes 12–14, a current flows through molecular structure 22. A conductivity measurement device 24 is placed in the series conduction path to measure current flow. In one embodiment, conductivity measurement device 24 is a low impedance ammeter. The current flow through molecular structure 22 is substantially the same current flowing through conductivity measurement device 24. Thus, conductivity measurement device 24 provides a signal representative of the conductivity of molecular structure 22.

Electronic controller 26 controls conductivity measurement system 10. In one embodiment, control system 26 is a computer system. Controller 26 sets the voltage of power supply 20. Controller 26 receives conductivity measurement readings from conductivity measurement device 24. Controller 26 controls the operation and movement of motion controller 30. Motion controller 30 is attached to electrode 14 by rod or screw drive 32. Controller 26 sends a signal to motion controller 30 which causes rod 32 to move in the X direction as shown in FIG. 1. Rod 32 can move electrode 14 closer to electrode 12, or farther away from electrode 12. In another embodiment, electrodes 12 and 14 may both be connected to motion controller 30 with rods like 32. In any case, motion controller 30 moves either or both of electrodes 12 and 14 relative to one another to close the gap or widen the gap between them. As will be explained, motion controller 30 can cause electrodes 12 and 14 to touch and make physical contact and can cause them to separate to a sufficient distance such that no molecule(s) can be joined between the electrodes.

Motion sensor or force detector 34 is attached to rod 32, or to electrode 14, to sense the motion of or force applied to the rod/electrode assembly. The force at which molecules break and the instance of one or more molecules having been broken is sensed and provided to controller 26 as a motion detection signal from motion sensor 34. The motion detection signal is useful in determining when the molecules joined between electrodes 12 and 14 break under the separation force. Controller 26 will have data as to the force, separation of electrodes, and instance in time when one or more molecules broke from the electrodes.

The apparatus shown in FIG. 1 can be used to measure the electrical and mechanical properties of one or more molecules. Probe electrodes 12–14 are placed in solution of the substance to be measured. Alternatively, the substance can be disposed on the electrodes, e.g. with an application tool, droplet, mist, gas, or evaporation. The molecules of the substance to be measured must have two terminal or end-groups which can bind to the gold electrodes. For example, thiol (sulfur group), pyridine, and isocyanide end-groups can form covalent bonds to electrodes 12–14. In one embodiment, the substance to be measured is 4,4'bipyridine, which has two thiol end-groups that can bind to the gold electrodes 12–14. Typically, a number of molecules of the substance to be measured form covalent bonds to the probe electrodes such that, when the electrodes are separated, many continuous molecular junctions are formed between electrode 12 and electrode 14. As will be discussed, conductivity measurement system 10 can confirm the formation of the molecular junctions and determine the number of molecules across the junction. In doing so, system 10 can isolate the situation when molecular structure 22 contains only a single molecule bridging the gap between probe electrodes 12–14.

Figure 2A:
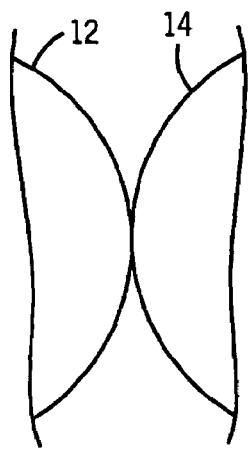
FIGS. 2a–2e illustrate first and second electrodes separating and breaking one or more molecular junctions.

In FIG. 2a, probe electrode 14 is brought into physical contact with probe electrode 12. A baseline calibration reading is taken from conductivity measurement device 24 and stored in controller 26. The baseline reading is the conductivity of the measurement system itself, with substantially zero resistance between the electrodes.

Figure 2B:
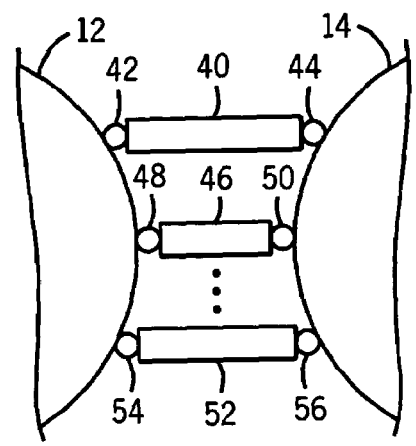

In FIG. 2b, probe electrode 14 is moved slightly away from probe electrode 12. A gap is formed between electrodes 12 and 14 by their relative motion away from one another. A molecular junction 40 is formed having end-groups 42 and 44 making contact with electrodes 12–14, respectively. In most cases, a molecular junction 46 is also formed having end-groups 48 and 50 making contact with electrodes 12–14, respectively, and a molecular junction 52 is formed having end-groups 54 and 56 making contact with electrodes 12–14, respectively. The end-groups of molecules 40, 46, and 52 of the substance to be measured are attached to the surfaces of probe electrodes 12–14 by covalent bonds.

In practice, a large number of molecular junctions may be formed across the gap when electrodes 12–14 are initially pulled apart. In the simplified view of FIGS. 2a–2e, only three molecular junctions are shown and illustrated as separate elements for ease of explanation. As will be seen in FIGS. 5a–5d, the molecules are likely grouped together or closely packed in a bundle.

With the gap set to its initial separation, a conductivity reading is taken by conductivity measurement device 24 and sent to controller 26. The reading is offset by the baseline reading of the measurement system. The measurement represents the conductivity of some unknown number of molecular junctions across the gap between electrodes 12–14.

Figure 2C:
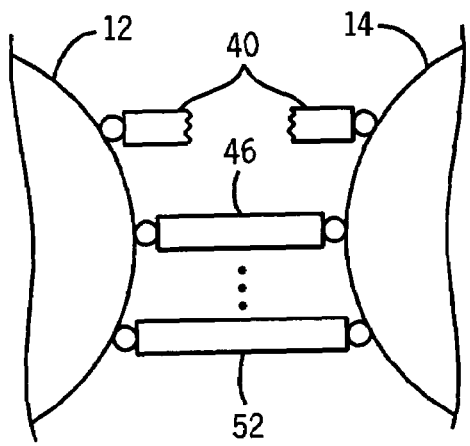

Controller 26 causes motion controller 30 to move rod 32 and electrode 14 to widen the gap between electrodes 12–14 in a discrete step. Another conductivity reading is taken and sent to controller 26. The reading is offset by the baseline reading of the measurement system. Motion controller 30 moves rod 32 again to further widen the gap between electrodes 12–14. Another conductivity reading is taken and sent to controller 26. Again, the reading is offset by the baseline reading of the measurement system. The process of widening the gap and taking readings continues in discrete steps, e.g., less than 1 nanometer (nm). At some point, at least one of the molecular junctions will break from the stress on the molecular bonds imposed from the increasing gap between the electrodes. In FIG. 2c, molecular junction 40 is shown as having been broken at distance D1. The next conductivity reading will show a smaller value as the total conductivity across the gap will have decreased by the absence of at least one of the molecular junctions.

Figure 2D:
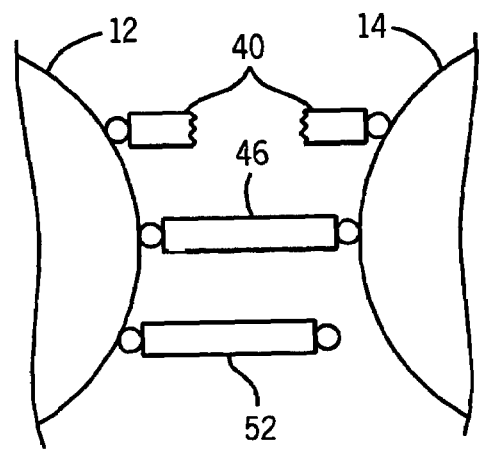

As the gap continues to widen, another molecular junction will break from the stress imposed from the increasing gap between the electrodes. In FIG. 2d, molecular junction 52 is shown as have broken at distance D2. In some cases, the molecule itself will break; in other cases, the end-group bond to the electrode will separate. The next conductivity reading will show an even smaller value as the total conductivity across the gap will have decreased by the absence of another molecular junction.

Figure 2E:
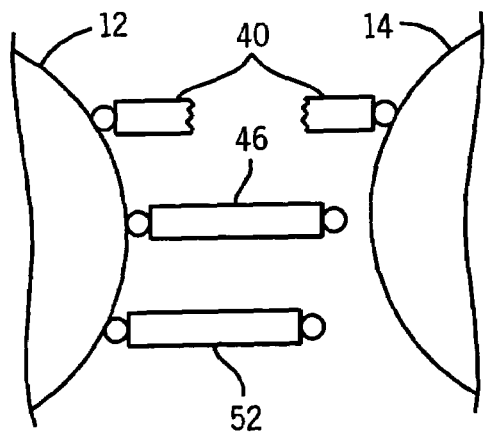

As electrodes 12–14 continue to separate in discrete steps, at some point in time, all molecular junctions across the gap between electrodes 12–14 will have broken. FIG. 2e illustrates the case of no more molecular junctions between electrodes 12–14 at distance D3. The conductivity measure will be zero. However, in most cases, the last non-zero conductivity measure just prior to the zero reading, will be the conductivity measure of one single molecule across the gap between electrodes 12–14.

The above testing is part of a calibration process in which probe electrodes 12–14 are repeatedly brought back together and moved apart until all molecular junctions are broken. The conductivity measurements are taken at each step of each test along the way. The test is repeated many times. With multiple sets of data (e.g., thousands), over a statistical distribution or histogram, the conductivity measure of a single molecule can be determined. The single molecule conductivity measure is statistically the last non-zero conductivity measure immediately prior to the zero conductivity reading. The single molecule is the last one to break. The same is true for two molecules, three molecules, and so on. The second to last non-zero conductivity measure statistically corresponds to two molecules; the third to last non-zero conductivity measure statistically corresponds to three molecules; and so on. By working backward from the case of no molecules across the gap, i.e., zero conductivity measure, the associated conductivity and I-V characteristics for one, two, three, etc., molecules can be determined over many tests in an accurate and repeatable manner.

The separation of electrodes may also be done in a continuous motion. The conductivity measure is sampled as the electrodes separate. The last non-zero reading before the zero reading corresponds to one single molecule across the gaps between electrodes 12–14.

Figure 3:
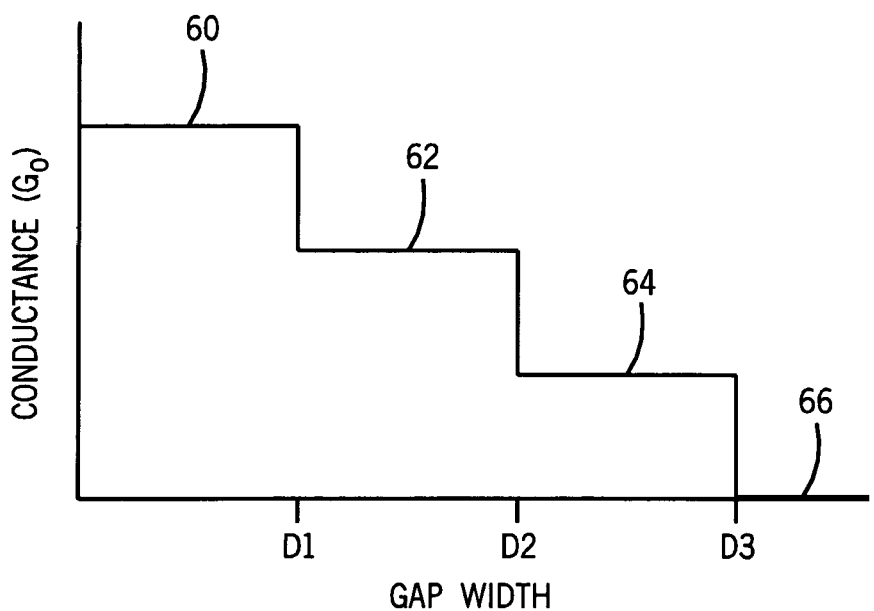
FIG. 3 illustrates a graphical representation of the conductivity measures.

FIG. 3 illustrates a graphical representation of the conductivity measures during the test. From the simplified representation in FIGS. 2a–2e, the graph shows the conductivity measure decreasing in discrete steps delineated by distances D1, D2, and D3. Plateau or step 60 corresponds to three molecular junctions across the gap as per FIG. 2b, step 62 corresponds to two molecular junctions across the gap as per FIG. 2c, step 64 corresponds to one molecular junction across the gap as per FIG. 2d, and step 66 corresponds to no molecular junctions across the gap as per FIG. 2e.

Figure 4:
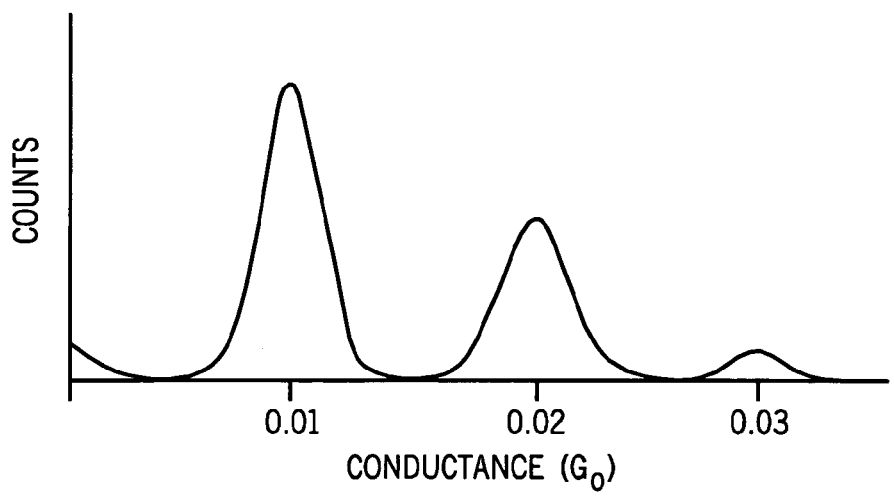
FIG. 4 illustrates a conductance histogram of the conductivity measures.

The conductance steps can also be seen as peaks in the conductance histogram of FIG. 4. In the absence of molecules, no peaks significantly below 1.0 $G_0$ are observed in the conductance histogram. The conductance peaks of different molecules are located at different conductance values. The conductance histogram constructed over many individual measurements reveals the peaks at approximately integer multiples of a fundamental value, i.e., 0.01 $G_O$ for 4,4'bipyridine in the present example. The fundamental value is identified as the conductance of a single molecule.

The motion detector 34 is also useful in determining force, separation, and timing of molecules breaking from electrodes 12 and 14. When a molecules breaks its covalent bonds under the separation force, motion detector 34 will sense the break and provide a motion detection signal to controller 26. The break dynamics generally involves a short oscillation as the bonds break and return to steady-state. The force required to break the molecular bonds and the signature of the detection signal are representative of the type of molecule under test and the molecular connection remaining.

The above description is given by way of simplification of the molecular junction and process of breaking molecular bonds. In actual practice, during the initial stage of the electrode separation process, a small gold neck is formed between the two electrodes due to large metallic cohesive energy, see FIG. 5a. As the electrodes are pulled apart, the neck becomes thinner and eventually reduced to the atomic scale, see FIG. 5b. The conductance decreases in discrete steps due to conductance quantization, e.g., in integer multiples of $G_O=2$ $e^2/h$, where h is Planck's constant. The conductance during the process is quantized as integer multiples of $G_O=2$ $e^2/h$, which signals that the contact is decreasing to the atomic scale. As electrode 14 is pulled further away to break individual molecules from contacting the electrodes, the conductivity value decreases in a sequence of steps as shown in FIG. 3. For the 4,4'bipyridine substance, the discrete steps may be 0.01 $G_O$, 0.02 $G_O$, 0.03 $G_O$, etc.

Figure 5A:
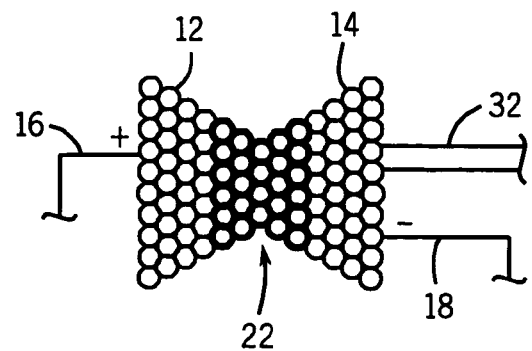
FIGS. 5a–5d illustrate an alternate representation of the electrodes separating and breaking one or more molecular junctions.
Figure 5B:
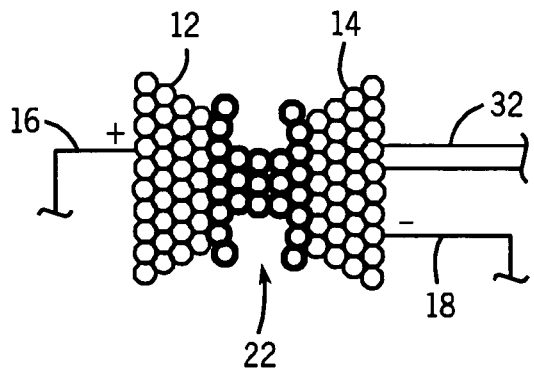
Figure 5C:
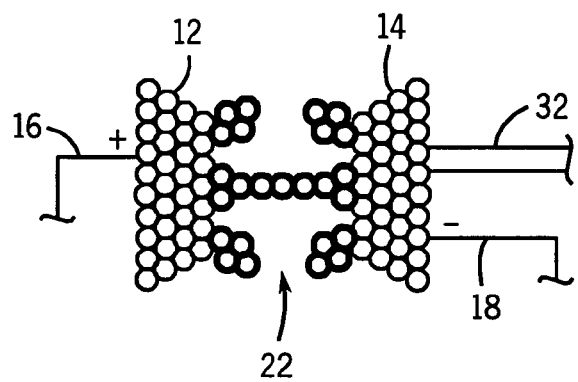
Figure 5D:
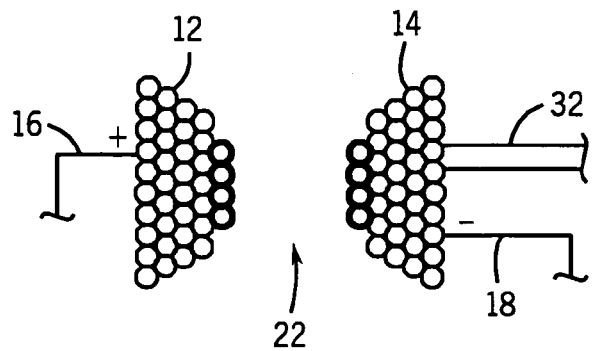

Once the conductivity measure reaches zero, then the conductivity and I-V characteristics of a single molecule can be determined by referring to the last non-zero conductivity measure just prior to the zero reading. FIG. 5c illustrates one molecular junction, i.e., one molecule, remaining between the electrodes. FIG. 5d illustrates the final step of breaking all molecular junctions.

Once the calibration process is complete, and the separation, conductivity, and force associate with one molecule is known, measurement system 10 can be used to analyze the electrical and physical characteristics of a single molecule. With the gap distance and conductivity of a single molecule having been determined from the calibration process as described above, the electrodes are separated to a distance such that a single molecule remains attached between electrodes 12 and 14. A single molecule will bridge the gap between electrodes 12–14 when the conductivity measure is the same as the last non-zero reading during the calibration process. Controller 26 can run a variety of electrical and physical tests on the single molecule to understand its conductivity, physical characteristics, and chemical makeup. The detailed measurements are useful in identifying the molecule under test and understanding its interaction with other molecules as discussed below.

Figure 6:
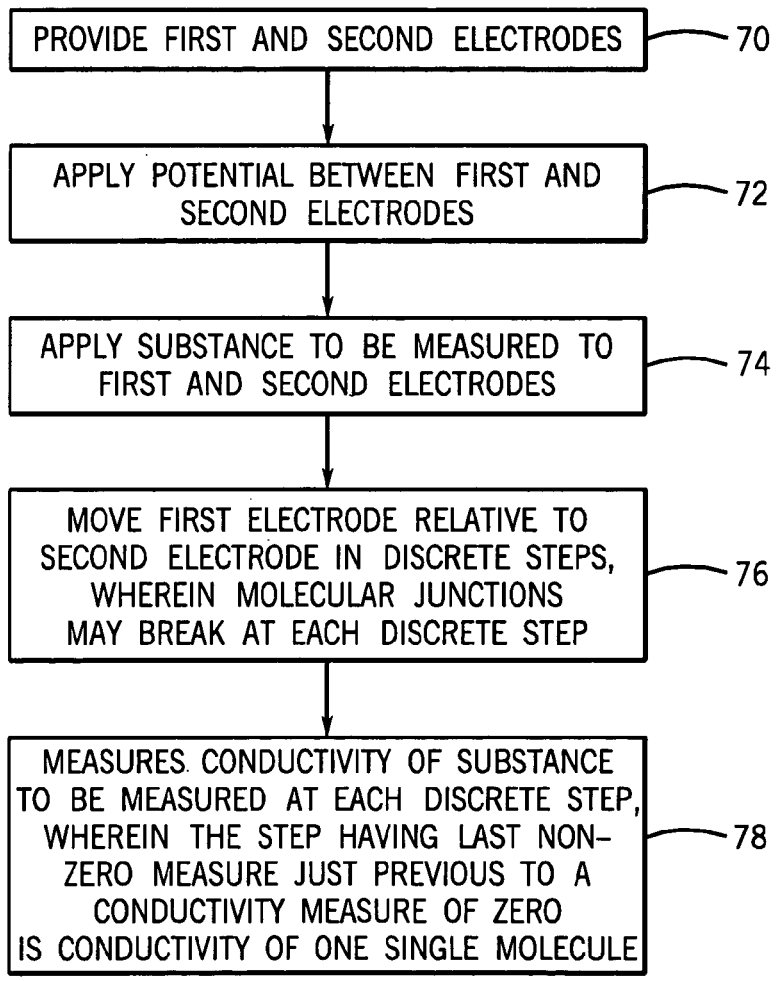
FIG. 6 illustrates the steps of measuring conductivity of a molecule.

The process of measuring conductivity of one molecule is shown in FIG. 6. Step 70 provides first and second electrodes. Step 72 applies a potential between the first and second electrodes. Step 74 applies a substance to be measured to the first and second electrodes. Step 76 moves the first electrode relative to the second electrode. Step 78 measures conductivity of the substance to be measured at a plurality of distances between the first and second electrodes. In a first step, the electrodes are brought in physical contact which forms a plurality of molecular junctions. In a second step, the electrodes are separated by a first distance which breaks a first molecular junction. In a third step, the electrodes are separated by a second distance which breaks a second molecular junction. A measure of conductivity is taken at each of the discrete steps. The step having the last non-zero measure just prior to a conductivity measure of zero is the conductivity of one single molecule.

In another embodiment, an electrochemical system is used to form the electrodes and vary the distance between them. A pair electrodes is fabricated on an oxidized silicon (Si) substrate. The electrodes are covered with a layer of silicon nitride (SiN) to reduce ionic leakage current which is need for measurements in aqueous solutions. The SiN layer also serves as a mask to etch the exposed $SiO_2$/Si area and create a narrow nm-scale trench over which the two electrodes are suspended. Using an electrochemical deposition or etching method, the gap is closed to form a point contact or nm-scale gap. The electrodes are exposed to a solution containing sample molecules of the substance to be measured to allow the molecules to adsorb on the point contact or bridge the nm-scale gap. The silicon substrate is bent in a controlled fashion so as to widen the gap and break one or more molecules across the gap. The conductance of one or more molecules can be determined as described above.

In another embodiment, an electrochemical gate can be formed using the molecular bridge. Referring to FIG. 1, a third electrode is positioned adjacent to the molecule(s) bridge the electrode gap. The third electrode is biased with a separate voltage from power supply 20. During the conductivity test, the third electrode controls the conductivity of the molecule(s) across the gap. The third electrode sets the molecule(s) across the gap between electrodes 12–14 to be conductive or non-conductive state or anywhere in-between, i.e. as a molecular transistor.

Understanding and quantifying the conductivity of molecules has a number of applications. The conductivity measurements and motion measurements are representative of chemical and biological information of the molecule. In one application, molecules can be identified by the conductivity measure. In another embodiment, the break force signature can be used to identify molecules. A database of conductivity and force measures of many different substances can be stored on controller 26. An unknown substance can be tested. The conductivity measure from the test sample may identify the substance from the computer database, or at least give an indication of its identification.

The conductivity measure can be used as a chemical sensor or biological sensor. Molecular recognition can be used with high accuracy and efficiency in biological systems, e.g., antibody-antigen binding, and can be used in the design of chemical and biological sensors. One type of molecule is known to readily bond to analyte species. A specific binding of an analyte (guest) species onto the molecule (host) can trigger changes in the electrical and mechanical properties of the molecule. A single host molecule is formed between the probe electrodes, with a given conductivity measure. When a guest molecule bonds to the host molecule, the conductivity measure will change. The change in conductivity corresponds to sensing the guest molecule. The magnitude of change in conductivity can also identify the type of guest molecule bonded to the host molecule. In one example, conductivity measurement system 10 can detect ions in water. Another example is molecular motors in muscle to oxygen binding hemoglobin in red blood cells.

In another application, the $NH_2$ and COOH side groups in the peptides can be protonated/deprotonated by varying the solution pH, which triggers a change in the conductance. The pH dependent conductance can be used to determine the pH of a local environment by measuring the conductance of a peptide. Another example is the specific binding of metal ions onto peptides, which can also induce a change in the conductance.

The conductivity measurement system can detect DNA sequencing and base pair mismatches. The conductance of DNA is highly sensitive to the sequence of the bases. One given sequence will have a different conductivity measure than another sequence. For GC-rich sequences, the conductance is inversely proportional to the molecular length, indicating a hopping mechanism for the charge transport. By inserting AT base pairs into the GC-rich sequences, the conductance decays exponentially with the length of the A:T region. In one example, in the sequence in CGCGAAT-TCGCG, replacing the second thymine (T) with guanine (G) yields CGCGAATGCGCG. The mutated sequence forms a duplex with two A:G mismatches. The presence of the mismatches results in a decrease in the conductance by a factor of about two. Thus, the change in conductivity has identified the DNA sequence and/or mismatch.

In molecular electronic applications, molecules can be identified and measured according to their electron transport properties. For example, the alkanedithiol molecule is linear and terminated with two thiols that can bind to the gold electrodes to form a molecular junction. The length can be easily varied by changing the number of carbon atoms in the molecule, which allowed for systematic study of the length dependence of the conductance. The I-V characteristics of alkanedithiol can be obtained from the conductance histograms at various bias voltages and then determine the I-V curve from the peak positions in the histograms at various voltages. When the conductivity measure indicates a single molecule is present, the electrode positions are held in place and I-V measurement is performed. For a tunneling dominated transport process, the conductance of the molecule decreases exponentially with the molecular length.

While one or more embodiments of the present invention have been illustrated in detail, the skilled artisan will appreciate that modifications and adaptations to those embodiments may be made without departing from the scope of the present invention as set forth in the following claims.

What is claimed is:

1. A method of measuring conductivity of a molecule, comprising:
    providing first and second electrodes;
    applying a potential between the first and second electrodes;
    applying a substance to be measured to the first and second electrodes;
    moving the first electrode relative to the second electrode, wherein a first step includes bringing the first and second electrodes in physical contact which forms a plurality of molecular junctions and a second step includes separating the first and second electrodes by a first distance which breaks a first molecular junction; and
    measuring conductivity of the substance to be measured at a plurality of distances between the first and second electrodes.

2. The method of claim 1, wherein the first electrode is moved relative to the second electrode in discrete steps.

3. The method of claim 1, wherein the first electrode is moved relative to the second electrode in a continuous motion.

4. The method of claim 1, wherein a third step includes separating the first and second electrodes by a second distance which breaks a second molecular junction.

5. The method of claim 4, wherein a fourth step includes separating the first and second electrodes by a third distance which breaks a third molecular junction.

6. The method of claim 5, wherein a measure of conductivity is taken at each of the steps.

7. The method of claim 6, wherein the step having the last non-zero measure just previous to a conductivity measure of zero is the conductivity of one single molecule.

8. A method of measuring conductivity of a molecule, comprising:
    applying a substance to be measured to first and second electrodes;
    moving the first electrode relative to the second electrode, wherein a first step includes bringing the first and second electrodes in physical contact which forms a plurality of molecular junctions and a second step includes separating the first and second electrodes by a first distance which breaks a first molecular junction; and
    measuring conductivity of the substance to be measured at a plurality of distances between the first and second electrodes, wherein the conductivity of one molecule corresponds to a last non-zero conductivity measurement prior to a zero conductivity measurement.

9. The method of claim 8, wherein the first electrode is moved relative to the second electrode in discrete steps.

10. The method of claim 8, wherein the first electrode is moved relative to the second electrode in a continuous motion.

11. The method of claim 8, wherein a third step includes separating the first and second electrodes by a second distance which breaks a second molecular junction.

12. The method of claim 11, wherein a measure of conductivity is taken at each step.

* * * * *